US010552930B1

(12) United States Patent
Jordan-Nowe et al.

(10) Patent No.: US 10,552,930 B1
(45) Date of Patent: Feb. 4, 2020

(54) ELECTRONIC PHYSICIAN REFERRAL MANAGEMENT SYSTEM AND METHODS

(71) Applicant: The Advisory Board Company, Washington, DC (US)

(72) Inventors: Cynthia Jordan-Nowe, Tucson, AZ (US); Colleen Cutshaw, Tucson, AZ (US); Leslie Perls, Tucson, AZ (US); Troy Hollar, Tucson, AZ (US); Anne Sarabia, Tucson, AZ (US)

(73) Assignee: The Advisory Board Company, Washington, DC (US)

( * ) Notice: Subject to any disclaimer, the term of this patent is extended or adjusted under 35 U.S.C. 154(b) by 542 days.

(21) Appl. No.: 13/646,533

(22) Filed: Oct. 5, 2012

Related U.S. Application Data

(60) Provisional application No. 61/543,619, filed on Oct. 5, 2011.

(51) Int. Cl.
    *G16H 80/00* (2018.01)
    *G06Q 50/22* (2018.01)
    *G16H 40/00* (2018.01)

(52) U.S. Cl.
    CPC ............. *G06Q 50/22* (2013.01); *G16H 80/00* (2018.01); *G16H 40/00* (2018.01)

(58) Field of Classification Search
    None
    See application file for complete search history.

(56) References Cited

U.S. PATENT DOCUMENTS

| 7,752,060 B2 * | 7/2010 | Hicks et al. ....................... 705/3 |
| 2007/0027718 A1 * | 2/2007 | Amerantes et al. ............... 705/3 |
| 2007/0083403 A1 * | 4/2007 | Baldwin ................ G06Q 10/10 |
| | | 705/346 |
| 2010/0262432 A1 * | 10/2010 | Benja-Athon ..................... 705/2 |
| 2011/0161096 A1 * | 6/2011 | Buehler et al. .................... 705/2 |

(Continued)

OTHER PUBLICATIONS

Mehrotra et al, Dropping the Baton: Specialty Referrals in the United States, Mar. 2011, The Milbank Quarterly, vol. 89, No. 1, pp. 39-68 (Year: 2011).*

*Primary Examiner* — Dennis W Ruhl
*Assistant Examiner* — William G Lultschik
(74) *Attorney, Agent, or Firm* — Bookoff McAndrews, PLLC (57) ABSTRACT

A physician referral management system is provided. The system includes a physician profile database, electronically accessible over at least one network system. The physician profile database stores physician profiles, each of which contain information associated with a physician. The system further includes a physician referral application which is hosted at least partially on a server and electronically accessible over at least one network system to a primary care physician device and a specialist physician device. The physician referral application is configured to facilitate a referral of a patient between the primary care physician device and the specialist physician device, and to allow a user of at least one of the primary care physician device and the specialist physician device to search for physicians based on information contained in the physician profiles. At least a portion of the physician profiles contains information relating to insurance plans accepted by particular physicians.

27 Claims, 5 Drawing Sheets

(56) References Cited

U.S. PATENT DOCUMENTS

2011/0191122 A1* 8/2011 Kharraz Tavakol ... G06Q 10/10
705/3
2013/0046551 A1* 2/2013 Vahle ................... G06F 19/328
705/2

* cited by examiner

ELECTRONIC PHYSICIAN REFERRAL MANAGEMENT SYSTEM AND METHODS

CROSS REFERENCE TO RELATED APPLICATIONS

This application claims priority from U.S. Provisional Application Ser. No. 61/543,619, filed Oct. 5, 2011, the contents of which are incorporated herein by reference.

FIELD OF THE DISCLOSURE

The present disclosure is generally related to physician referrals of patients to other physicians or specialists, and more particularly is related to an electronic physician referral management system.

BACKGROUND OF THE DISCLOSURE

Primary care physicians have traditionally made patient referrals based on personal knowledge and individual preference. Typically, a primary care physician will rely on his or her own personal knowledge, however limited and/or inaccurate, of specialists when deciding to whom to refer a particular patient. Referrals are an important source of patients, and thus revenues, for many medical practices. Thus, for many health care organizations, such as Health (Hospital) Systems or Accountable Care Organizations, there is a financial interest in preventing patient referrals to providers outside of the organization, and to increasing referrals coming into the organization. Out-migration of patients from hospital systems and other healthcare networks, i.e. away from their employed and/or contracted physicians, can result in millions of dollars in lost revenue every year.

Changes in the primary care landscape, including growing patient volume and the increasing primacy of insurance coverage, may cause complications to the traditional methods of making patient referrals. Moreover, recent changes in the economics of providing healthcare (i.e., decreased revenues generated on a per patient basis) may require that primary care practices and specialists increase productivity in order to prevent lost revenues.

Currently, some limited electronic referral systems exist. However, such systems often require the owner of the record to populate the information of their referring partners (name, phone, fax, etc.), are specific to a particular electronic medical record or technology platform and are geographically limited. Moreover, the data included in such systems is often limited to publicly or commercially available data.

The currently available referral systems and techniques are inefficient, as the referring practices' staff often must contend with multiple, complex and cumbersome processes for finding the right specialists and making referrals. Such referral processes take a significant amount of time and limit the focus on patient care quality. Furthermore, such systems make referrals without knowledge of insurance data.

Thus, a heretofore unaddressed need exists in the industry to address the aforementioned deficiencies and inadequacies.

SUMMARY OF THE DISCLOSURE

Embodiments of the present disclosure provide a system for coordinating physician referrals. Briefly described, in architecture, one embodiment of the system, among others, can be implemented as follows. A physician referral management system includes a physician profile database, which is electronically accessible over at least one network system. The physician profile database stores a plurality of physician profiles, each of the plurality of physician profiles containing information associated with a physician. A physician referral application is hosted at least partially on a server and is electronically accessible over at least one network system to a primary care physician device and a specialist physician device. The physician referral application is configured to facilitate a referral of a patient between the primary care physician device and the specialist physician device, and the physician referral application is further configured to allow a user of at least one of the primary care physician device and the specialist physician device to search for physicians based on information contained in the physician profiles. At least a portion of the plurality of physician profiles contains information relating to insurance plans accepted by particular physicians.

In another embodiment, a physician referral management process is provided that includes the steps of: providing a physician profile database, electronically accessible over at least one network system, the database storing a plurality of physician profiles, each of the plurality of physician profiles containing information associated with a physician; providing a physician referral application, hosted at least partially on a server and electronically accessible over at least one network system to a primary care physician device and a specialist physician device; allowing a user of the primary care physician device to initiate a search for physicians based on information contained in the physician profiles; and facilitating a referral of a patient initiated by the primary care physician device to the specialist physician device. At least a portion of the plurality of physician profiles contains information relating to insurance plans accepted by particular physicians.

In yet another embodiment, a non-transitory computer readable medium is provided that contains instructions for providing a physician referral management process enabled at least in part on a processor of a computerized device, wherein a physician profile database is electronically accessible by the processor, the database storing a plurality of physician profiles, each of the plurality of physician profiles containing information associated with a physician, and a physician referral application is hosted at least partially on a server and electronically accessible over at least one network system to a primary care physician device and a specialist physician device, the instructions, which when executed by the processor, performing the steps of: allowing a user of the primary care physician device to initiate a search for physicians based on information contained in the physician profiles; and facilitating a referral of a patient initiated by the primary care physician device to the specialist physician device, wherein at least a portion of the plurality of physician profiles contains information relating to insurance plans accepted by particular physicians.

In another embodiment, a physician referral management process is provided that includes the steps of: providing an electronic message to a user of a physician referral application, in response to the user attempting at least one of a search for, and a referral to, an out-of-network physician, the electronic message requiring the user to respond with a reason for attempting the at least one of a search for, and a referral to, an out-of-network physician; receiving, by the physician referral application, the user's response; and facilitating, by the physician referral application, the at least one of a search for, and a referral to, an out-of-network physician.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Many embodiments of the disclosure may take the form of computer-executable instructions, including algorithms executed by a programmable computer. However, the disclosure can be practiced with other computer system configurations as well. Certain aspects of the disclosure can be embodied in a special-purpose computer or data processor that is specifically programmed, configured or constructed to perform one or more of the computer-executable algorithms described below. Accordingly, the term "computer" as generally used herein refers to any data processor and includes Internet appliances, hand-held devices (including palm-top computers, wearable computers, cellular or mobile phones, multi-processor systems, processor-based or programmable consumer electronics, network computers, minicomputers) and the like.

The disclosure also can be practiced in distributed computing environments, where tasks or modules are performed by remote processing devices that are linked through a communications network. Moreover, the disclosure can be practiced in Internet-based or cloud computing environments, where shared resources, software and information may be provided to computers and other devices on demand. In a distributed computing environment, program modules or subroutines may be located in both local and remote memory storage devices. Aspects of the disclosure described below may be stored or distributed on computer-readable media, including magnetic and optically readable and removable computer disks, fixed magnetic disks, floppy disk drive, optical disk drive, magneto-optical disk drive, magnetic tape, hard-disk drive (HDD), solid state drive (SSD), compact flash or non-volatile memory, as well as distributed electronically over networks including the cloud. Data structures and transmissions of data particular to aspects of the disclosure are also encompassed within the scope of the disclosure.

Figure 1:
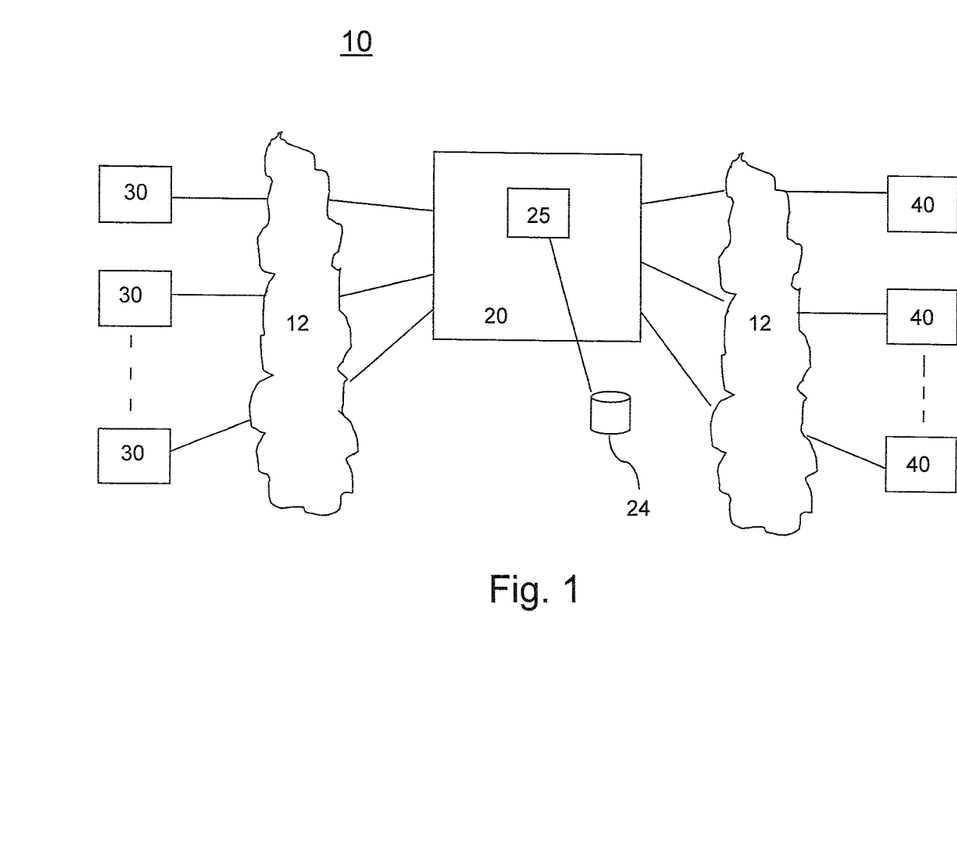
FIG. 1 is a schematic illustration of a physician referral management system, in accordance with a first exemplary embodiment of the present disclosure.

FIG. 1 is a schematic illustration of a physician referral management system 10, in accordance with a first exemplary embodiment of the present disclosure. The physician referral management system 10, which may also be referred to as 'system 10', includes a physician referral application 25, electronically accessible over at least one network system 12 and hosted at least partially on a server 20. At least one primary care physician device 30 is positioned to access the physician referral application 25 and at least one specialist physician device 40 is positioned to access the application 25.

The server 20 may be or include any database capable of storing and/or providing access to information, such as an electronic database, a computer and/or computerized server, database server or generally any network host capable of storing data and connected to any type of data network. Further, the server 20 may include or be a part of a distributed network or cloud computing environment. Any type of electronic and/or computerized device that is capable of storing information may be included as the server 20, and is considered within the scope of this disclosure. The server 20 may include computer-readable storage media, and a processor for processing data and executing algorithms, including any of the processes and algorithms set forth in this disclosure. The physician referral application 25 is electronically accessible over at least one network system 12. The network system 12 may include any type of network infrastructure, such as the Internet, or any other wired, wireless and/or partially wired network. The server 20, application 25 and network system 12 may include a variety of hardware and software components to provide successful functioning of the server 20 and the application 25, as is well-known within the art. Further, any features, characteristics, designs and/or functions that are known within the art may be included with the system 10 to further enhance its efficiency.

The at least one primary care physician device 30 may be any device that is capable of communicating with the application 25, for example via a network system 12, and may be operated by any primary care physician, medical doctor, nurse, medical staff or other medical professional, or any representative thereof. The at least one specialist physician device 40 may be any device that is capable of communicating with the application 25, for example via a network system 12, and may he operated by any specialist physician, medical doctor, nurse, medical staff or other medical professional, or any representative thereof. Any number of primary care physician devices 30 and specialist physician devices 40 may use the system 10 at any given time. The primary care physician device 30 and specialist physician device 40 may access the application 25 through a variety of ways, including through a computerized device in communication with the system 10 over a network system. For example, the primary care physician device 30 and/or specialist physician device 40 may be any computer, including any personal computer, Internet appliance, hand-held device (including palm-top computers, wearable computers, cellular or mobile phones, multi-processor systems, processor-based or programmable consumer electronics, network computers, minicomputers) and the like. Other ways of accessing the application 25 may include using a telephone. One or more input devices, such as a keyboard or mouse, may be used to transmit information to and/or request information from the application 25 by either of the primary care physician device 30 and/or the specialist physician device 40.

The physician referral application 25 may be fully or partially hosted on the server 20. The physician referral application 25 may include any tool, device, system, process or combination thereof, which assists or makes possible a physician referral of a patient to another physician. For example, the physician referral application 25 may facilitate a patient referral from a primary care physician using device 30 to a specialist physician using device 40. The application 25 may include any computer-readable memory or databases, which may be stored in any computer-readable medium, and may be accessible by a computer processor. The application 25 may further include or access computer program instructions which may cause a processor to perform any algorithms and/or functions which may be described in this disclosure.

The system 10 further includes a physician profile database 24. The application 25 has access to the physician profile database 24, which may be fully or partially hosted on the server 20, or may be hosted elsewhere and otherwise accessible to the application 25. The physician profile database 24 stores profiles of physicians (primary care and/or specialists) and/or medical practices that may refer or receive patient referrals through the system 10. Each physician and/or medical practice within the system has a unique profile.

The profiles contain contact information (e.g., name, address, phone number, etc.) for the physician and/or medical practice, as well as information relating to insurance plans that are accepted by the physician and/or medical practice. The profile information may further include information relating to whether the physician is "in-network" or "out-of-network," i.e., whether the physician is associated with any particular healthcare organization, such as any Accountable Care Organization or other health care provider organizations. Additionally or alternatively, the physician profile database 24 may be partitioned or otherwise include two separate sets of profile data: in-network physician profiles and out-of-network physician profiles.

The profile information may further include, for example, information such as: the physician's name, address, gender, age, training, ranking information, education, medical specialty, awards, malpractice information, administrative referral contact information, place of business, and/or any other information associated with the physician and/or medical practice and any other information which may be relevant to referring physicians and/or physicians receiving patient referrals through the system 10.

The profile information may be composed from publicly available information, as well as from privately developed and gathered information. Further, the profile information may be input by a physician utilizing a primary care physician device 30 or a specialist physician device 40, for example by inputting requested information to the system 10 upon registering as a physician in the system 10. A physician utilizing a primary care physician device 30 or specialist device 40 may be able to add, delete or modify profile information for that physician in the physician profile database 24.

The application 25 may include or provide access to a web or network-based software platform, including a graphical user interface or webpage which provides interactive access to the system 10 to a user of a primary care physician device 30 and/or a specialist physician device 40. Alternatively or additionally, a primary care physician device 30 and/or specialist physician device 40 may include software providing access to the system 10.

In practice, physicians (whether primary care or specialists) often need to refer a patient to another physician, e.g., to a specialist for specialized care. Using the system 10, the referring primary care physician, a medical referral clerk or the like uses a primary care physician device 30 to access the physician referral application 25. The physician referral application 25 may be a web-based application and may require authorization information, such as username and password, before allowing the user to access the application 25.

Figure 2:
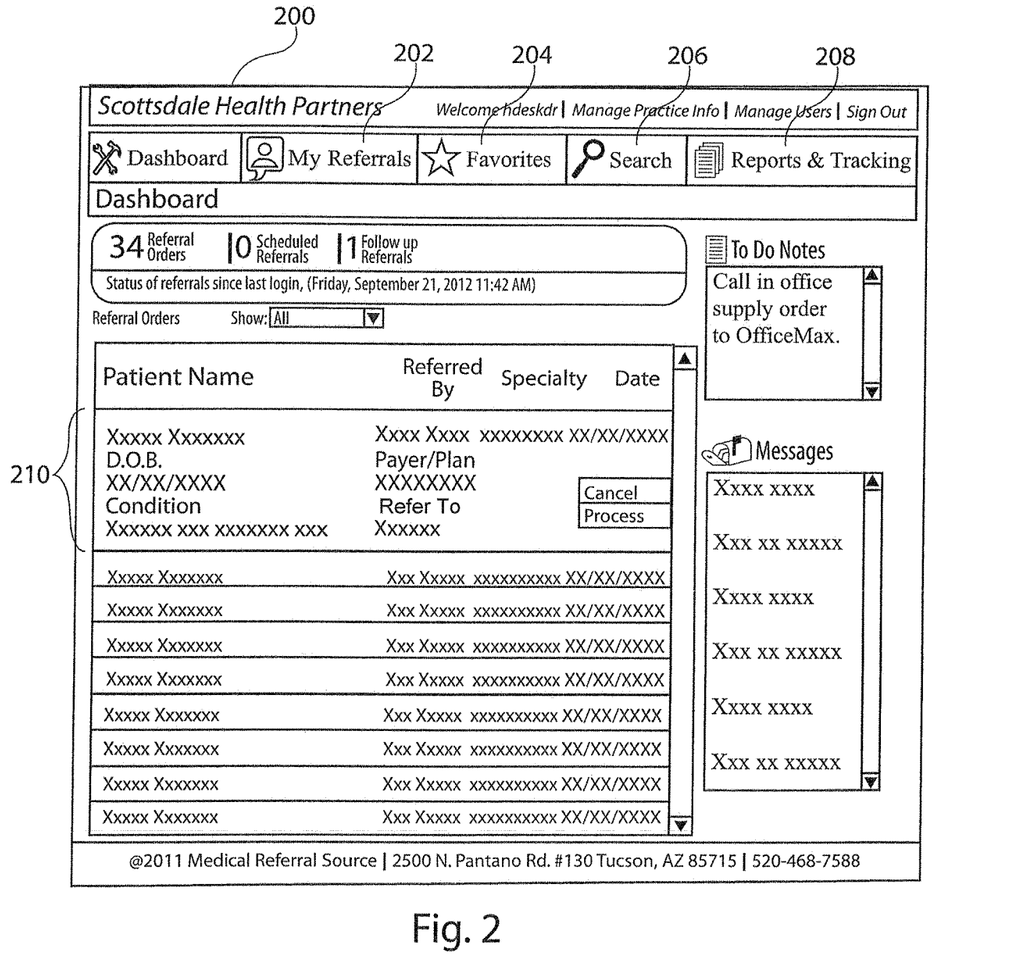
FIG. 2 is an illustration of a webpage which may be utilized by the system of FIG. 1, in accordance with the first exemplary embodiment of the present disclosure.

FIG. 2 illustrates a portion of a webpage 200 which may be utilized by the system 10. The webpage 200, for example, may be included in and/or provided by the physician referral application 25. The webpage 200 may be accessible by the at least one primary care physician device 30 and/or the at least one specialist physician device 40. For example, the webpage 200 may be the "dashboard" or the interface provided by the application 25 to a user after successfully logging into the application 25. The webpage 200 may display information related to the status of referrals, including for example, the number of referrals ordered, the number of referrals received and/or the number of pending follow-up referrals, through the system 10.

The physician referral application 25 may be integrated into the primary care physician's and/or the specialist physician's electronic health record system, such that when a physician orders a referral (e.g., a primary care physician refers a patient to a specialist physician through the system 10), healthcare information from the referred patient's electronic health record may be transmitted or otherwise made available through the application 25 to the specialist physician receiving the referred patient. As shown in FIG. 2, a referred patient's electronic health record information 210 may be displayed on the webpage 200. The webpage 200 provides links to other subpages or features of application 25, such as: "My Referrals" 202, "Favorites" 202, "Search" 206, and "Reports & Tracking" 208.

Using the "My Referrals" 202 feature, a user such as staff in primary care physician offices may use the physician referral application 25 to make and track patient referrals into, or coming from, specialists or other healthcare providers' offices. The listing of "My Referrals" can be sorted by date and/or time and may include information regarding the patient, the status of the referral and so on.

The "Favorites" 204 feature allows the staff in the primary care physician's office to identify providers they frequently refer patients to and allows them to make referrals to them without going through the formal search process.

The dashboard webpage 200 may further include a "Prior Authorization" feature which assists the staff or other user of the system 10 in obtaining prior authorizations from insurance carriers when needed. For example, the prior authorization feature may include links which take the user to the prior authorization website of the insurance carrier for a particular patient. Information relating to all insurance plans in a given market, including prior authorization websites for each, may be loaded into or otherwise accessible by the application 25. Thus, before referring a patient to a particular specialist physician, the referring primary care physician or her referral clerk may use the application to first determine whether the specialist accepts the type of insurance carried by the patient, and may further perform a prior authorization to ensure, for example, that the patient is insured for the care provided by the specialist.

The "Search" 206 feature allows a user of the at least one primary care physician device 30 and/or the at least one specialist physician device 40 to search and find listings of specialists based on many search criteria. The search criteria may be pulled from profile information for physicians stored in the physician profile database 24. For example, the user may search for physicians based on accepted insurance plans, whether the physician is in-network or out-of-network, location of the physician, gender, age, training, ranking information, education, medical specialty, awards, and/or any other information associated with the physician and/or medical practice and any other information which may be relevant to referring physicians and/or physicians receiving patient referrals. The search results may be displayed as a list of physicians, and may further include information for each physician as may be included in the physician profiles. The search results may be displayed in a randomized order, so that all physicians matching the search criteria are given equal opportunity, or as may be required by relevant statutes, laws or policies.

The application 25 may be configured to only provide access to, or to preferentially provide access to, "in-network" physicians, i.e., those who are associated with a particular healthcare organization, such as a particular Accountable Care Organization or a particular hospital system. For example, the application 25 may be configured to display search results for only those physicians that are associated with the particular healthcare organization, or to rank or otherwise display higher in the search result order those physicians that are associated with the particular healthcare organization. Additionally or alternatively, the application 25 may provide search results separately within two or more predefined groups of physicians. For example, the search results may be provided as two separate groups of physicians: those who are "in-network" physicians, and those who are "out-of-network" physicians. In such a case, the physicians within each group of search results may be displayed in a random order. The predefined groups of physicians may be ranked or displayed based on preference such that, for example, the group of "in-network" physicians is displayed with a higher rank or more prominently provided to the user, while the group of "out-of-network" physicians is given a lower rank.

Once a specialist physician is found to whom the user wishes to refer the patient, the user may utilize the application 25 to send an online referral or a fax referral to the specialist provider. When the user makes an online referral, the application 25 will transmit a message to the referred specialist's dashboard webpage. That is, when the referred specialist (or her staff, etc.) logs into the application 25 using a specialist physician device 40, the specialist will see a new referral, which may include information about the referred patient such as name, referring physician, insurance information, condition for which the patient was referred, date of referral, and the like. Referrals received by a specialty physician office, for example as displayed to a specialist physician device 40 when accessing the webpage 200, may be searched to find patient referrals by name, status, referred from, referred by, referral date and so on.

A fax referral may be made through the application 25, in which case the application 25 may utilize a fax number for the referred specialist physician, which may be included in the specialist's physician profile, to transmit a fax to the specialist indicating that the patient has been referred. The fax may similarly include information about the referred patient such as name, referring physician, insurance information, condition for which the patient was referred, date of referral, and the like. Moreover, the application 25 may allow a referring user to fax other information or documents accessible to the application 25 (such as, for example, clinical information or electronic health record information available to the application 25) to the referred specialist, along with the faxed referral.

The physician referral application 25 may further include a communication tool which enables online communication between users of primary care physician devices 30 and/or specialist physician devices 40. For example, using the communication tool of application 25, a referral clerk using a primary care physician device 30 can send a message directly to the specialist's office indicating that a referral has been made, details of the referred patient, an inquiry as to whether the specialist has available appointments, or any other message. The communication tool may facilitate online communication between users of the application 25, and may allow, for example, one physician to contact other physician offices regarding patient referrals. The communications made through the communication tool may include chat, email, SMS or text messages, video, voice or any other type of electronic communication, and further may be encrypted and securely stored in the application 25.

The application 25 may further allow a physician profile to be printed, for example by any printer connected to a primary care physician device 30 and/or a specialist device 40. Thus, a referring physician or her staff can print the profile of the referred specialist physician for the patient to view. The profile may include special instructions for the practice.

The application 25 may further allow a user to make a referral to providers who are not yet registered in the system 10, i.e. who do not have a physician profile or other information in the physician profile database 24. In such a case, the referring user may enter information for the physician to whom the user wishes to refer a patient, which may include, for example, name, address, email address, phone number, fax number, specialty, and the like. By entering such information for the referred physician, the referred physician now has a physician profile which may be stored in the physician profile database 24 and may thus become available to accept referrals from other users of the system 10.

The application 25 may further allow a referring user to indicate an electronic signature is attached to the referral (thereby making it an "order" for care).

The "Reports & Tracking" 208 feature of the application 25 allows specialists who receive referrals through the application 25 to create reports and track referral trends for their practice. The reports may include information such as who their referrals come from, from what geographical area or healthcare organizations, what types of patients and/or conditions are they being referred for, number and frequency of referrals and/or any other referral information which may be available through the system 10.

As discussed above, the physician referral application 25 may be configured to restrict searches of physicians to only include, or to preferentially display, in-network physicians. This may be preferable to some users, including healthcare organizations such as Accountable Care Organizations which may prefer to refer patients to physicians within their own organization. Additionally, the application 25 may be configured to display to a user any physician, whether in-network or out-of-network, and to allow the user to select and refer a patient to any physician within the system 10.

Figure 3:
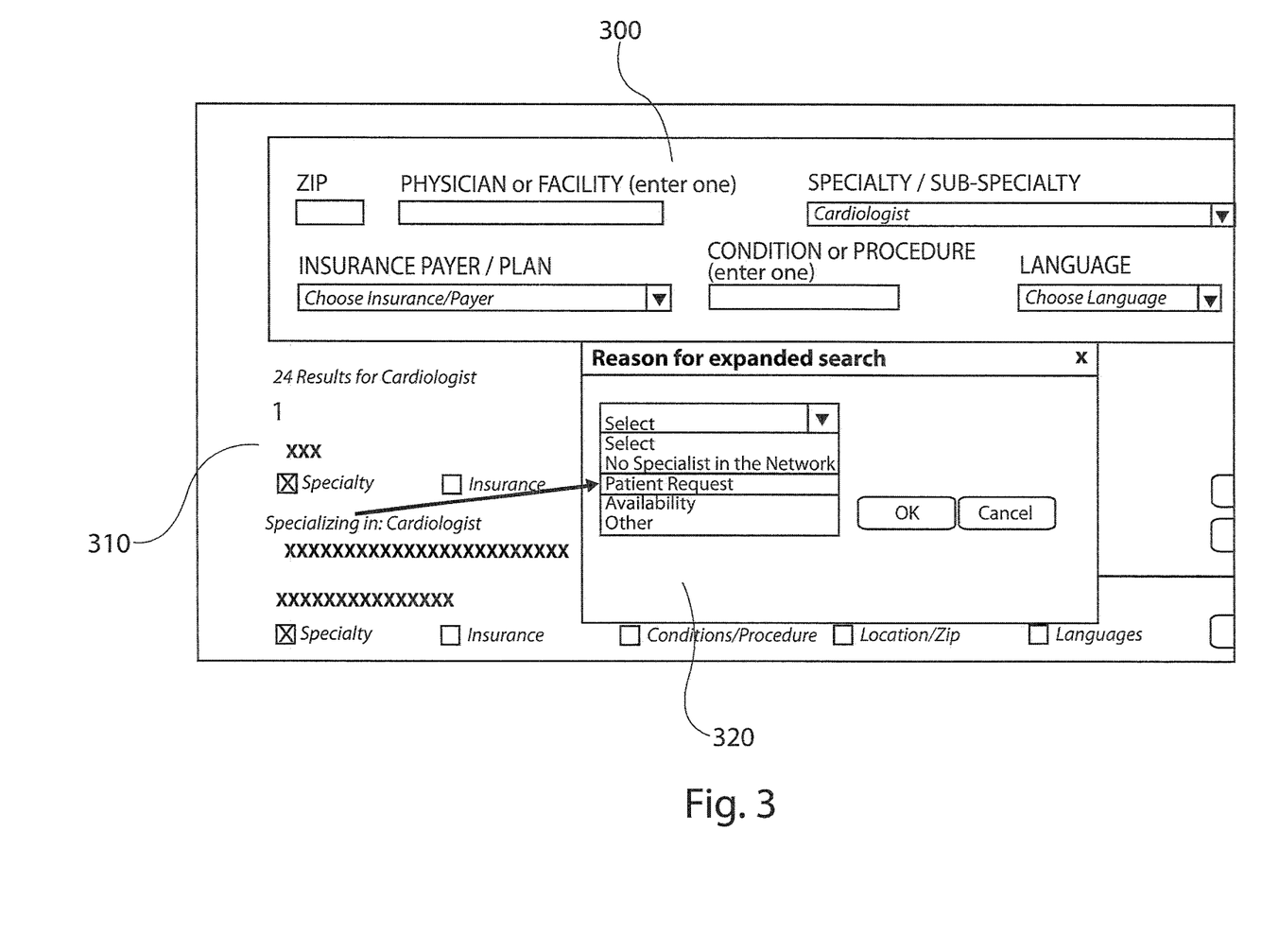
FIG. 3 is an illustration of a webpage which may be utilized by the system of FIG. 1, in accordance with the first exemplary embodiment of the present disclosure.

FIG. 3 illustrates a portion of a webpage 300 which may be utilized by the system 10 and may be, for example, a subpage or webpage which is accessible to a user through the dashboard webpage 200 and may be included in and/or provided by the physician referral application 25. As shown in FIG. 3 one or more out-of-network physicians 310 may be displayed on the webpage 300, whether as the result of a search, by utilizing the "Favorites" 204 feature, or through any other means for displaying one or more physicians through the system 10. When a user of a primary care physician device 30 or a specialist physician device 40 attempts to make a patient referral to the out-of-network physician 310, the application 25 may cause the webpage 300 to provide a message 320 requiring the user to provide a reason as to why the user is attempting to refer the patient to an out-of-network physician. After providing a reason for making the out-of-network referral, the referral may be facilitated to the out-of-network physician 310 by the application 25. The reason may be provided, for example, by selecting one of a number of reasons that loaded into the application 25, or by typing or otherwise inputting textual information explaining the reason.

Further, the physician referral application 25 may he configured to provide a message 320 when the user attempts to search for out-of-network physicians. That is, upon attempting a search of out-of-network physicians, the webpage 300 may provide a message 320 which requires the user to provide a reason as to why the user is attempting to search for an out-of-network physician. After providing a reason for the out-of-network search, the application 25 may display search results for the out-of-network physicians.

Information provided by a user as the reason for referring to, or searching for, out-of-network physicians may be provided to healthcare organizations or medical practices in order to allow such organizations or practices to better understand and/or track the sources and impacts of referrals to out-of-network physicians.

The system 10 may further provide advertising opportunities, which may allow, for example, users such as physicians and/or medical practices to increase their exposure and referral sources. For example, the application 25 may cause the webpage 200 and/or any subpages to display electronic advertisements for users wishing to receive referrals. Further, the application 25 may allow third parties, such as insurance companies, to advertise over the system 10. Insurance companies may, for example, pay an advertising fee and the application 25 may cause the webpage 200 to display advertisements of the insurance company to users of the system 10.

As specified herein, the system 10 may include a number of other features to enhance the design, use or functionality of the system 10 to provide better physician referrals. These additional features may include functional or aesthetic components within the application 25, such as website components, software based automation or the ability to tailor the system 10 to the preferences of a particular primary care physician or specialist physician using the system 10.

Figure 4:
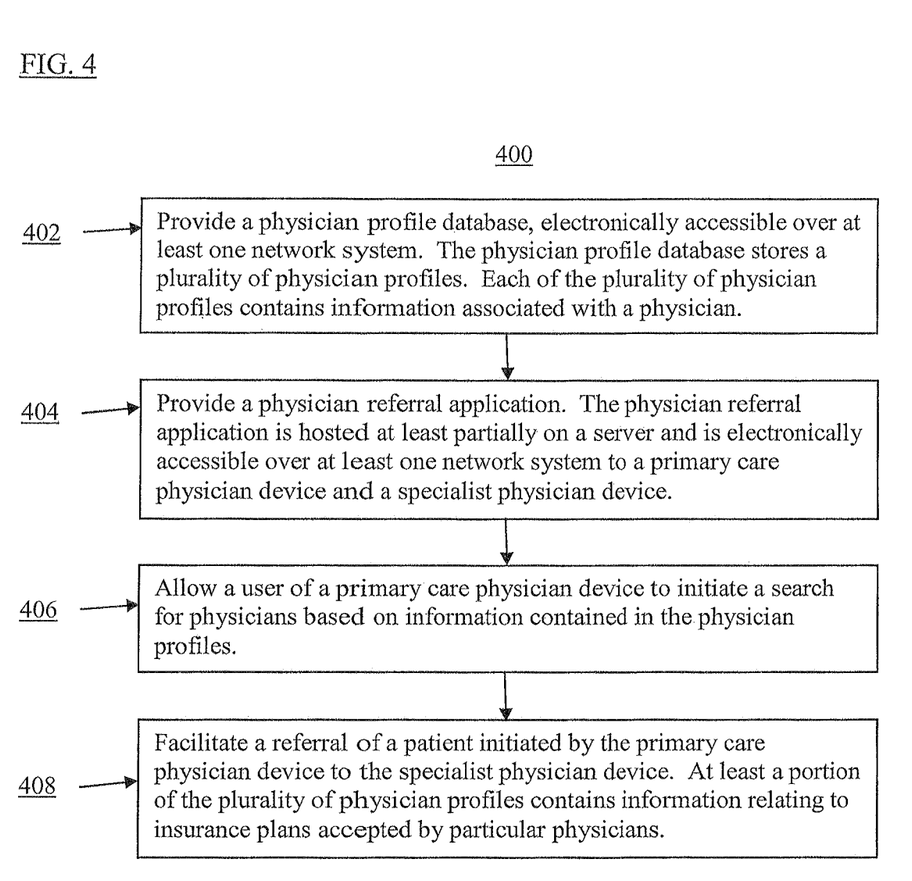
FIG. 4 is a flowchart illustrating a physician referral management process, in accordance with the first exemplary embodiment of the disclosure.

FIG. 4 is a flowchart 400 illustrating a physician referral management process in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present invention in which functions may be executed out of order from that shown or discussed, including substantially concurrently in reverse order, depending on the functionality involved, as would be understood by those reasonably skilled in the art of the present invention.

As shown in block 402, a physician profile database is provided. The database is electronically accessible over at least one network system 12 and stores a plurality of physician profiles. Each of the plurality of physician profiles contains information associated with a physician. As shown in block 404, a physician referral application 25 is provided. The physician referral application 25 is hosted at least partially on a server 20 and is electronically accessible over at least one network system 12 to a primary care physician device 30 and a specialist physician device 40.

In operation, a user utilizes a primary care physician device 30 and/or a specialist physician device 40 to access the physician referral application 25 through a network 12. The application 25 may, for example, display a webpage 200 which provides access to the system 10. As shown at block 406, a user of a primary care physician device 30 and/or specialist device 40 is allowed to initiate a search for physicians based on information contained in the physician profiles. At block 408, a referral of a patient initiated by the primary care physician device to the specialist physician device 40 is facilitated. At least a portion of the plurality of physician profiles contains information relating to insurance plans accepted by particular physicians.

Figure 5:
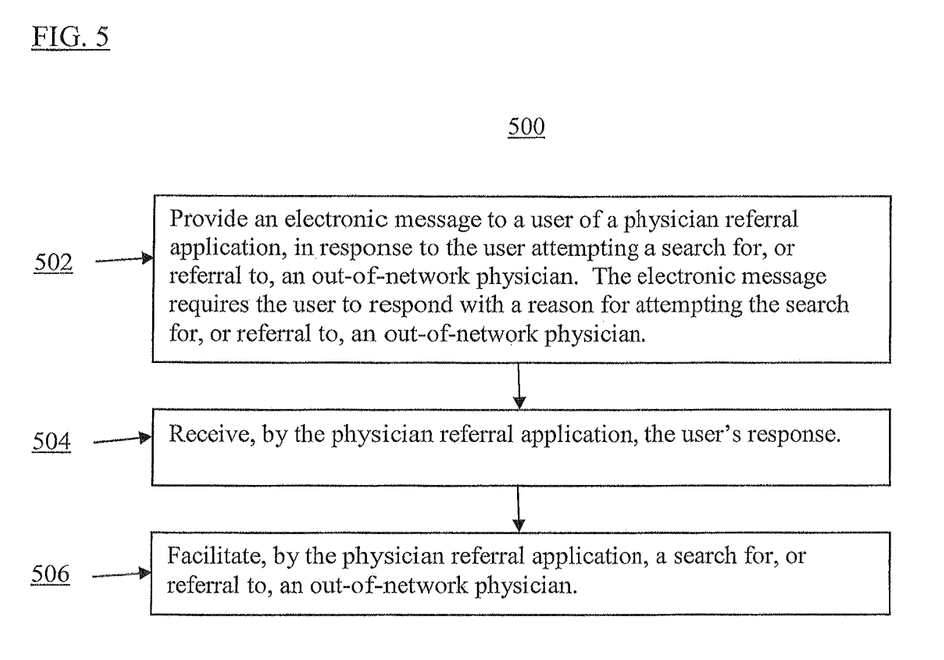
FIG. 5 is a flowchart illustrating a physician referral management process in accordance with an exemplary embodiment of the disclosure.

FIG. 5 is a flowchart 500 illustrating a physician referral management process in accordance with an exemplary embodiment of the disclosure. As shown in block 502, an electronic message 320 is provided to a user of a physician referral application 25, in response to the user attempting a search for, or referral to, an out-of-network physician. The electronic message 320 requires the user to respond with a reason for attempting the search for, or referral to, an out-of-network physician. At block 504, the physician referral application 25 receives the user's response. At block 506, the physician referral application 25 facilitates a search for, or referral to, an out-of-network physician.

A feature and advantage of the present disclosure which results from the adoption and integration of electronic medical record technology is that such technology helps medical organizations and practices manage clinical workflows. Thus, in addition to providing provider-to-provider electronic referral capabilities, which may result in users having more efficient and higher revenue generating practices, the systems and methods disclosed herein provide users the ability to better manage clinical workflows. These two systems usually are independent of each other.

Also, the ability to restrict searches of physicians to only those that are in-network, or alternatively to preferentially display physicians that are in-network, allows Accountable Care Organizations to preferentially provide referrals to providers within their own organization, while further providing physicians with the ability to refer patients to out-of-network providers when an in-network provider is not available. Moreover, by providing physicians with the ability to create and edit their own physician profiles, complete profiles of physicians may be generated, and may include information such as the insurance plans accepted, accurate UPIN and state license numbers, which is not available for sale in the market currently.

After a referral is made via the system 10, the referral form, containing relevant clinical and administrative data may then be available to both the primary care and the specialty practice via the system 10. The system 10 allows a primary care physician to attach a portion of a medical record document to the referral form allowing the specialist practice to view the medical record, for example when logging into the application 25. When purchased by a healthcare organization such as a hospital system or Accountable Care Organization, the physician referral application 25 may be configured to provide specific results (custom search hierarchy) for primary care providers when searching for a specialist provider.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. For example, while the disclosure primarily describes referrals as being primary care provider to specialist referrals, referrals may also be made between specialists (e.g., using specialist physician devices) and/or between primary care physicians (e.g., using primary care physician devices). All such modifications and variations are intended to be included herein within the scope of this disclosure and the present disclosure and protected by the following claims.

What is claimed is:

1. A physician referral management system comprising:
at least one data storage device storing instructions for physician referral management; and
at least one processor configured to execute the instructions to perform a method comprising:
storing, at a physician profile database electronically accessible over at least one network system, a plurality of physician profiles, each of the plurality of physician profiles containing information associated with a physician, wherein the information associated with the physician includes information defining insurance plans accepted by the physician and whether the physician is a member of a particular healthcare organization;
displaying, through an online dashboard of a physician referral application, indicia defining a number of referrals ordered, a number of referrals received, and a number of pending follow-up referrals made, since a prior log-in into the physician referral application, the physician referral application being a web-based application hosted at least partially on a server and having access to the physician profile database;
facilitating, through the online dashboard of the physician referral application, a referral of a patient between a primary care physician device and a specialist physician device;
receiving, through the online dashboard of the physician referral application, a search request for physicians based on information contained in the physician profiles;
in response to the search request, determining a first predefined group of physicians based on a first grouping criteria, and determining a second predefined group of physicians based on a second grouping criteria;
determining a rank of the first grouping criteria relative to the second grouping criteria;
displaying, on the online dashboard of the physician referral application, the first predefined group of physicians in random order, relative to other members of the first predefined group of physicians, based on the first grouping criteria;
displaying, on the online dashboard of the physician referral application, the second predefined group of physicians in random order, relative to other members of the second predefined group of physicians, based on the second grouping criteria;
displaying the first predefined group of physicians relative to the second predefined group of physicians based on the rank of the first grouping criteria relative to the second grouping criteria, the first grouping criteria corresponding to membership in the particular healthcare organization, the second grouping criteria corresponding to out-of-network physicians who are not members of the particular healthcare organization;
in response to receiving a request to perform a search for and referral to an out-of-network physician, displaying on the online dashboard of the physician referral application an electronic message indicating the request is for an out-of-network physician, said electronic message configured to prompt the user to respond with a reason for requesting the search for and the referral to the out-of-network physician;
providing a referral data record, associated with the referral to the out-of-network physician, to both the primary care physician device and the specialist physician device; and
generating, for a specialist physician associated with the specialist physician device, analytics data comprising a number and frequency of referrals, and compiled statistics on referral providers.

2. The physician referral management system of claim 1, wherein the physician referral application is located remotely from the physician profile database.

3. The physician referral management system of claim 1, wherein the information associated with a physician includes at least four of: the physician's phone number, gender, age, training, ranking information, education, medical specialty, awards received, malpractice information, administrative referral contact information, and place of business.

4. The physician referral management system of claim 1, wherein the physician referral application is configured to allow a user of at least one primary care physician device to search for physicians based on whether the physician is a member of the particular healthcare organization.

5. The physician referral management system of claim 1, wherein the physician profile information comprises information received from users of at least one of the primary care physician device and the specialist physician device.

6. The physician referral management system of claim 1, wherein the physician referral application is further configured to access at least a portion of patients' electronic health records, and to provide the specialist physician device access to at least a portion of a patient's electronic health records when such patient has been referred to the specialist physician associated with the specialist physician device.

7. The physician referral management system of claim 1, wherein the physician referral application is further configured to track patient referrals made by and received from at least one of the primary care physician device and the specialist physician device.

8. The physician referral management system of claim 1, wherein the physician referral application is further configured to provide the primary care physician device and the specialist physician device with access to patient insurance prior authorization information.

9. The physician referral management system of claim 1, wherein the physician referral application is further configured to transmit a referral communication to a specialist via fax.

10. The physician referral management system of claim 1, wherein the physician referral application is configured to facilitate electronic communication between primary care physician and specialist physician devices.

11. The physician referral management system of claim 1, wherein the physician referral application is configured to provide referral trends.

12. A computer-implemented method for physician referral management, comprising:
   storing, at a physician profile database electronically accessible over at least one network system, a plurality of physician profiles, each of the plurality of physician profiles containing information associated with a physician, wherein the information associated with the physician includes information defining insurance plans accepted by the physician and whether the physician is a member of a particular healthcare organization;
   displaying, through an online dashboard of a physician referral application, indicia defining a number of referrals ordered, a number of referrals received, and a number of pending follow-up referrals made, since a prior log-in into the physician referral application, the physician referral application being a web-based application hosted at least partially on a server and having access to the physician profile database;
   facilitating, through the online dashboard of the physician referral application, a referral of a patient between a primary care physician device and a specialist physician device;
   receiving, through the online dashboard of the physician referral application, a search request for physicians based on information contained in the physician profiles;
   in response to the search request, determining a first predefined group of physicians based on a first grouping criteria, and determining a second predefined group of physicians based on a second grouping criteria;
   determining a rank of the first grouping criteria relative to the second grouping criteria;
   displaying, on the online dashboard of the physician referral application, the first predefined group of physicians in random order, relative to other members of the first predefined group of physicians, based on the first grouping criteria;
   displaying, on the online dashboard of the physician referral application, the second predefined group of physicians in random order, relative to other members of the second predefined group of physicians, based on the second grouping criteria;
   displaying the first predefined group of physicians relative to the second predefined group of physicians based on the rank of the first grouping criteria relative to the second grouping criteria, the first grouping criteria corresponding to membership in the particular healthcare organization, the second grouping criteria corresponding to out-of-network physicians who are not members of the particular healthcare organization;
   in response to receiving a request to perform a search for and referral to an out-of-network physician, displaying on the online dashboard of the physician referral application an electronic message indicating the request is for an out-of-network physician, said electronic message configured to prompt the user to respond with a reason for requesting the search for and the referral to the out-of-network physician;
   providing a referral data record, associated with the referral to the out-of-network physician, to both the primary care physician device and the specialist physician device; and
   generating, for a specialist physician associated with the specialist physician device, analytics data comprising a number and frequency of referrals, and compiled statistics on referral providers.

13. The method of claim 12, wherein the information associated with a physician comprises at least four of: the physician's phone number, email address, gender, age, training, ranking information, education, medical specialty, awards received, malpractice information, administrative referral contact information, and place of business.

14. The method of claim 12, further comprising:
   receiving input information for a physician profile from at least one of the primary care physician device and the specialist physician device.

15. The method of claim 12, further comprising:
   accessing at least a portion of patients' electronic health records; and
   providing to the specialist physician device access to at least a portion of a patient's electronic health records when such patient has been referred to the specialist physician associated with the specialist physician device.

16. The method of claim 12, further comprising:
   facilitating electronic communication between primary care physician and specialist physician devices.

17. The method of claim 12, further comprising:
   tracking patient referrals made by and received from the primary care physician device and the specialist physician device.

18. The method of claim 12, further comprising:
   providing the primary care physician device and the specialist physician device with access to patient insurance prior authorization information.

19. The method of claim 12, further comprising:
   facilitating a referral communication to be transmitted to a specialist via fax.

20. The method of claim 12, wherein the instructions, when executed by the processor, further perform the step of providing referral trends.

21. A non-transitory computer readable medium comprising instructions that, when executed by at least one processor of at least one computerized device, performs a method of physician referral management comprising:
   storing, at a physician profile database electronically accessible over at least one network system, a plurality of physician profiles, each of the plurality of physician profiles containing information associated with a physician, wherein the information associated with the physician includes information defining insurance plans accepted by the physician and whether the physician is a member of a particular healthcare organization;
   displaying, through an online dashboard of a physician referral application, indicia defining a number of referrals ordered, a number of referrals received, and a number of pending follow-up referrals made, since a prior log-in into the physician referral application, the physician referral application being a web-based application hosted at least partially on a server and having access to the physician profile database;

facilitating, through the online dashboard of the physician referral application, a referral of a patient between a primary care physician device and a specialist physician device;

receiving, through the online dashboard of the physician referral application, a search request for physicians based on information contained in the physician profiles;

in response to the search request, determining a first predefined group of physicians based on a first grouping criteria, and determining a second predefined group of physicians based on a second grouping criteria;

determining a rank of the first grouping criteria relative to the second grouping criteria;

displaying, on the online dashboard of the physician referral application, the first predefined group of physicians in random order, relative to other members of the first predefined group of physicians, based on the first grouping criteria;

displaying, on the online dashboard of the physician referral application, the second predefined group of physicians in random order, relative to other members of the second predefined group of physicians, based on the second grouping criteria;

displaying the first predefined group of physicians relative to the second predefined group of physicians based on the rank of the first grouping criteria relative to the second grouping criteria, the first grouping criteria corresponding to membership in the particular healthcare organization, the second grouping criteria corresponding to out-of-network physicians who are not members of the particular healthcare organization;

in response to receiving a request to perform a search for and referral to an out-of-network physician, displaying on the online dashboard of the physician referral application an electronic message indicating the request is for an out-of-network physician, said electronic message configured to prompt the user to respond with a reason for requesting the search for and the referral to the out-of-network physician;

providing a referral data record, associated with the referral to the out-of-network physician, to both the primary care physician device and the specialist physician device; and generating, for a specialist physician associated with the specialist physician device, analytics data comprising a number and frequency of referrals, and compiled statistics on referral providers.

22. The non-transitory computer readable medium of claim 21, wherein the instructions, when executed by the processor, further perform the step of:
receiving input information for a physician profile from at least one of the primary care physician device and the specialist physician device.

23. The non-transitory computer readable medium of claim 21, wherein the instructions, when executed by the processor, further perform the steps of:
accessing at least a portion of patients' electronic health records; and
providing to the specialist physician device access to at least a portion of a patient's electronic health records when such patient has been referred to the specialist physician associated with the specialist physician device.

24. The non-transitory computer readable medium of claim 21, wherein the instructions, when executed by the processor, further perform the step of:
facilitating electronic communication between primary care physician and specialist physician devices.

25. The non-transitory computer readable medium of claim 21, wherein the instructions, when executed by the processor, further perform the step of:
tracking patient referrals made by and received from the primary care physician device and the specialist physician device.

26. The non-transitory computer readable medium of claim 21, wherein the instructions, when executed by the processor, further perform the step of:
providing the primary care physician device and the specialist physician device with access to patient insurance prior authorization information.

27. The non-transitory computer readable medium of claim 21, wherein the instructions, when executed by the processor, further perform the step of:
facilitating a referral communication to be transmitted to a specialist via fax.

* * * * *